US012188063B2

United States Patent
Ueda et al.

(10) Patent No.: US 12,188,063 B2
(45) Date of Patent: Jan. 7, 2025

(54) ENZYMATIC MUTANT SUITABLE FOR HOMOGENEOUS IMMUNOASSAY METHOD

(71) Applicant: INSTITUTE OF SCIENCE TOKYO, Tokyo (JP)

(72) Inventors: Hiroshi Ueda, Tokyo (JP); Jiulong Su, Tokyo (JP); Tetsuya Kitaguchi, Tokyo (JP); Yuki Ohmuro, Tokyo (JP)

(73) Assignee: INSTITUTE OF SCIENCE TOKYO, Tokyo (JP)

( * ) Notice: Subject to any disclaimer, the term of this patent is extended or adjusted under 35 U.S.C. 154(b) by 633 days.

(21) Appl. No.: 17/428,477

(22) PCT Filed: Jan. 23, 2020

(86) PCT No.: PCT/JP2020/002264
§ 371 (c)(1),
(2) Date: Aug. 4, 2021

(87) PCT Pub. No.: WO2020/162203
PCT Pub. Date: Aug. 13, 2020

(65) Prior Publication Data
US 2022/0119789 A1    Apr. 21, 2022

(30) Foreign Application Priority Data
Feb. 8, 2019  (JP) ................ 2019-021450

(51) Int. Cl.
*C12N 9/24* (2006.01)
*C07K 19/00* (2006.01)
(Continued)

(52) U.S. Cl.
CPC ............ *C12N 9/2402* (2013.01); *C07K 19/00* (2013.01); *C12N 15/62* (2013.01); *C12Q 1/34* (2013.01); *C12Y 302/01031* (2013.01)

(58) Field of Classification Search
CPC ...... C12N 9/2402; C12N 15/62; C07K 19/00; C12Q 1/34; C12Y 302/01031
See application file for complete search history.

(56) References Cited

U.S. PATENT DOCUMENTS

| 2003/0092894 A1 | 5/2003 | Antonsson et al. |
| 2012/0252071 A1 | 10/2012 | Greif et al. |
| 2017/0248597 A1 | 8/2017 | Muench et al. |

FOREIGN PATENT DOCUMENTS

| JP | 2002-502363 A | 1/2002 |
| JP | 2017-534055 A | 11/2017 |

(Continued)

OTHER PUBLICATIONS

Flores et al., "Increasing the Thermal Stability of an Oligomeric Protein, Beta-glucuronidase", Journal of Molecular Biology, 2002, vol. 315, pp. 325-337.

(Continued)

*Primary Examiner* — Thomas J. Visone
*Assistant Examiner* — Georgiana C Reglas
(74) *Attorney, Agent, or Firm* — Birch, Stewart, Kolasch & Birch, LLP

(57) ABSTRACT

Provided as a mutant of β glucuronidase suitable for homogeneous immunoassays is a β glucuronidase mutant, wherein, in the amino acid sequence of *Escherichia coli* β glucuronidase, methionine at position 516 is substituted with lysine, and tyrosine at position 517 is unsubstituted or substituted with a non-tyrosine aromatic amino acid.

18 Claims, 7 Drawing Sheets

Specification includes a Sequence Listing.

(51) Int. Cl.
*C12N 15/62* (2006.01)
*C12Q 1/34* (2006.01)

(56) References Cited

FOREIGN PATENT DOCUMENTS

WO   WO-2017130610 A1 *  8/2017   ............. C07K 16/00
WO   WO-2018204343 A1 * 11/2018   ....... A61K 39/39591

OTHER PUBLICATIONS

Geddie et al., "Antibody-induced Oligomerization and Activation of an Engineered Reporter Enzyme", Journal of Molecular Biology, 2007, vol. 369, pp. 1052-1059.
International Search Report for PCT/JP2020/002264 (PCT/ISA/210) mailed on Apr. 21, 2020.
Su et al., "Creation of stable and strictly regulated enzyme switch for signal-on immunodetection of various small antigens", Journal of Bioscience and Bioengineering, Jun. 21, 2019, vol. 128, No. 6, pp. 677-682.
Written Opinion of the International Searching Authority for PCT/JP2020/002264 (PCT/ISA/237) mailed on Apr. 21, 2020.
English translation of the International Preliminary Report on Patentability (Form PCT/IPEA/409) for International Application No. PCT/JP2020/002264, dated Apr. 1, 2021.

\* cited by examiner

ENZYMATIC MUTANT SUITABLE FOR HOMOGENEOUS IMMUNOASSAY METHOD

REFERENCE TO ELECTRONIC SEQUENCE LISTING

This application contains a Sequence Listing which has been submitted electronically in .txt format and is hereby incorporated by reference in its entirety. Said .XML copy, created on Jul. 26, 2021, is named "2021-08-04_Sequence-Listing_3749-0185PUS1.txt" and is 20,802 bytes in size. The sequence listing contained in this .txt file is part of the specification and is hereby incorporated by reference herein in its entirety.

TECHNICAL FIELD

The present invention relates to a mutant of β glucuronidase suitable for homogeneous immunoassays, a fusion protein containing the mutant, and a method for detecting an antigen and antigen detection kit using the fusion protein.

BACKGROUND ART

Currently, immunoassays have been increasingly becoming important measurement techniques in clinical diagnoses. Not only improvement of sensitivity/specificity but also speedup/simplification of measurement has become a major factor in employing a particular immunoassay. In current mainstream immunoassays, a sandwich method is used in detection of a protein biomarker as the measurement principle, and a competition method is used in small molecule detection as the measurement principle. In both cases, however, enzymatic immunoassays, which involve several cycles of reaction and washing followed by measurement primarily of the activity of an enzyme used for labeling, are often used, causing a problem of need for effort and several hours of time for measurement. In contrast to these, homogeneous immunoassays, which involve mixing a sample and a measurement reagent to react together and detecting, allow simple and quick measurement, and hence have been attracting attention in recent years.

Regarding homogeneous immunoassays, the present inventors have recently reported a method using a mutant of β glucuronidase (GUS) (Patent Literature 1). While GUS exhibits the activity through formation of a tetramer, the presence of a mutation in the amino acid sequence (e.g., a mutation that, in Escherichia coli GUS, substitutes methionine at position 516 and tyrosine at position 517 with lysine and glutamic acid, respectively) lowers the intermonomer affinity, and GUS is allowed to form a dimer but prevented from forming a tetramer in normal condition. The measurement method utilizes such a characteristic of GUS, and uses two fusion proteins: a fusion protein containing an antibody VH domain and a mutant of GUS, and a fusion protein containing an antibody VL domain and a mutant of GUS. The principle of the measurement method is as follows. If no antigen is present in a sample, the interaction between the VH domain and the VL domain remains weak, and hence a dimer of the mutant of GUS linked to the VH domain and that linked to the VL domain also remains as it is and scarcely forms a tetramer. If an antigen is present in a sample, in contrast, the interaction between the VH domain and the VL domain is enhanced, and this interaction allows a dimer of the mutant of GUS linked to the VH domain and that linked to the VL domain to bind together to form a tetramer, which in turn exhibits activity. Therefore, the amount of an antigen in a sample can be measured by measuring the activity of GUS.

CITATION LIST

Patent Literature

[Patent Literature 1] International Publication No. WO 2017/130610

SUMMARY OF INVENTION

Technical Problem

Use of the GUS mutant described in Patent Literature 1 enables detection of an antigen with high sensitivity; however, detection methods with higher sensitivity are required for use in the field of medicine such as clinical diagnoses. The present invention was made in such circumstances, and an object of the present invention is to provide a GUS mutant that enables antigen detection with higher sensitivity.

Solution to Problem

The present inventors diligently examined to solve the above problems to find that, in the antigen detection method using a GUS mutant described in Patent Literature 1, use of a GUS mutant, wherein, in the amino acid sequence of Escherichia coli GUS, methionine at position 516 and tyrosine at position 517 are substituted with lysine and tryptophan, respectively, results in remarkably increased GUS activity (signal value) in the presence of an antigen and remarkably decreased GUS activity (background value) in the absence of an antigen, and completed the present invention on the basis of this finding.

Specifically, the present invention provides (1) to (8) in the following.

(1) A mutant of β glucuronidase, wherein, in the sequence of Escherichia coli β glucuronidase, methionine at position 516 is substituted with lysine, and tyrosine at position 517 is unsubstituted or substituted with a non-tyrosine aromatic amino acid.

(2) The β glucuronidase mutant according to (1), wherein, in the amino acid sequence of Escherichia coli β glucuronidase, tyrosine at position 517 is substituted with tryptophan.

(3) The β glucuronidase mutant according to (1) or (2), wherein, in the amino acid sequence in Escherichia coli β glucuronidase, further, asparagine at position 27 is substituted with tyrosine, phenylalanine at position 51 is substituted with tyrosine, alanine at position 64 is substituted with valine, aspartic acid at position 185 is substituted with asparagine, isoleucine at position 349 is substituted with phenylalanine, glycine at position 368 is substituted with cysteine, asparagine at position 369 is substituted with serine, tyrosine at position 525 is substituted with phenylalanine, glycine at position 559 is substituted with serine, lysine at position 567 is substituted with arginine, phenylalanine at position 582 is substituted with tyrosine, glutamine at position 585 is substituted with histidine, and glycine at position 601 is substituted with aspartic acid.

(4) The β glucuronidase mutant according to (3), wherein, in the amino acid sequence of Escherichia coli β glucuronidase, cysteine at position 368 is substituted with serine.

(5) A fusion protein containing: the β glucuronidase mutant according to any one of (1) to (4); a linker peptide bound to the β glucuronidase mutant; and an antibody VH domain or VL domain bound to the linker peptide.
(6) A nucleic acid encoding the fusion protein according to (5).
(7) A method for detecting an antigen in a sample, comprising the steps of: bringing the sample into contact with the fusion protein containing an antibody VH domain according to (5) and the fusion protein containing an antibody VL domain according to (5); and detecting tetramer formation of the β glucuronidase mutant through change in enzyme activity.
(8) An antigen detection kit including the fusion protein containing an antibody VH domain according to (5) and the fusion protein containing an antibody VL domain according to (5).
(9) A fusion protein containing: the β glucuronidase mutant according to any one of (1) to (4); a linker peptide bound to the β glucuronidase mutant; and a heavy-chain antibody VH domain bound to the linker peptide.
(10) A nucleic acid encoding the fusion protein according to (9).
(11) A method for detecting an antigen in a sample, comprising the steps of: bringing the sample into contact with the fusion protein according to (9); and detecting tetramer formation of the R glucuronidase mutant through change in enzyme activity.
(12) An antigen detection kit comprising the fusion protein according to (9).

The present specification includes the contents of the specification and/or drawings of Japanese Patent Application No. 2019-021450, a Japanese patent application on the basis of which the priority of the present application is claimed.

Advantageous Effects of Invention

The present invention provides a mutant of GUS suitable for homogeneous immunoassays.

DESCRIPTION OF EMBODIMENTS

Figure 1:
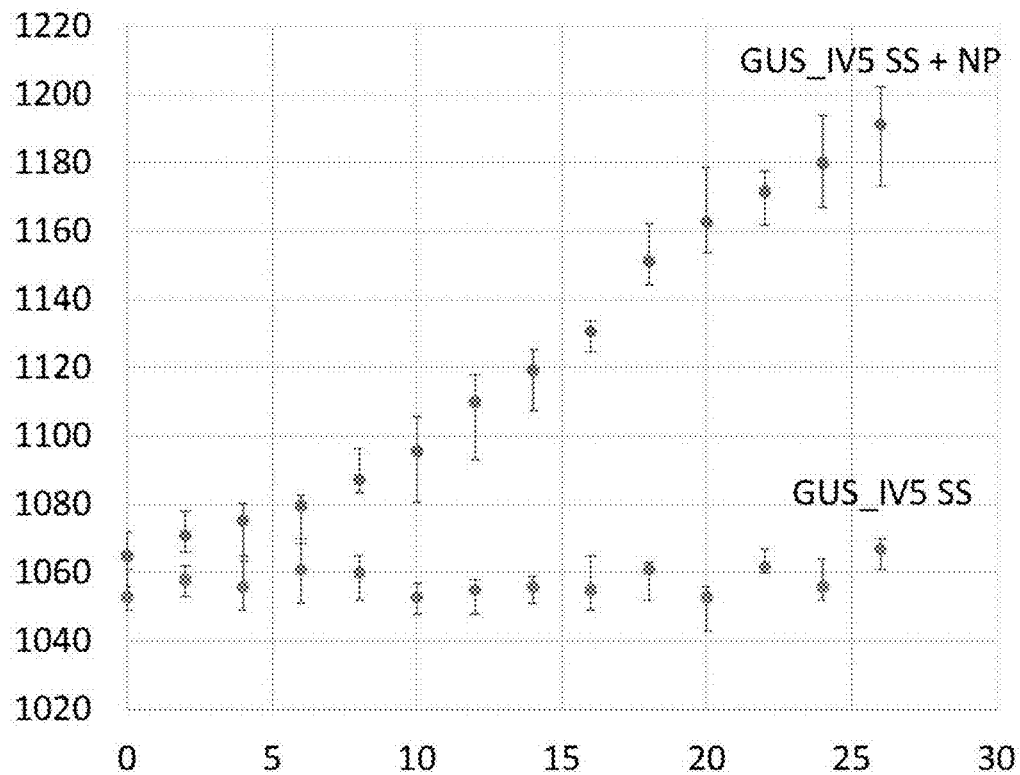
FIG. 1 shows a graph representing the activity of VH/VL (NP)-GUS(IV-5)KE in the presence and absence of NP (N=3).

Hereinafter, the present invention will be described in detail.
(1) β Glucuronidase Mutant The β glucuronidase mutant according to the present invention is characterized in that, in the amino acid sequence of *Escherichia coli* β *glucuronidase*, methionine at position 516 is substituted with lysine, and tyrosine at position 517 is unsubstituted or substituted with a non-tyrosine aromatic amino acid.

Here, the "non-tyrosine aromatic amino acid" is, for example, tryptophan or phenylalanine.

It is adequate that tyrosine at position 517 in the amino acid sequence of *Escherichia coli* β glucuronidase be unsubstituted or substituted with a non-tyrosine aromatic amino acid; however, it is preferable that tyrosine at position 517 in the amino acid sequence of *Escherichia coli* β *glucuronidase be substituted with tryptophan*.

A mutation other than the above mutations may be introduced into the β glucuronidase mutant according to the present invention. Examples of such mutations include mutations that improve thermal stability. What mutation should be introduced to improve the thermal stability of β glucuronidase is described in many pieces of literature (e.g., Flores H. et al., J. Mol. Biol. 315, 325-37, 2002), and hence those skilled in the art could specify a mutation according to the literature. Specific examples of mutations that improve the thermal stability of β glucuronidase in the amino acid sequence of *Escherichia coli* β *glucuronidase may include a mutation that substitutes asparagine at position* 27 with tyrosine, a mutation that substitutes phenylalanine at position 51 with tyrosine, a mutation that substitutes alanine at position 64 with valine, a mutation that substitutes aspartic acid at position 185 with asparagine, a mutation that substitutes isoleucine at position 349 with phenylalanine, a mutation that substitutes glycine at position 368 with cysteine, a mutation that substitutes asparagine at position 369 with serine, a mutation that substitutes tyrosine at position 525 with phenylalanine, a mutation that substitutes glycine at position 559 with serine, a mutation that substitutes lysine at position 567 with arginine, a mutation that substitutes phenylalanine at position 582 with tyrosine, a mutation that substitutes glutamine at position 585 with histidine, and a mutation that substitutes glycine at position 601 with aspartic acid (these mutations are those contained in the mutant IV-5 in Flores H. et al., J. Mol. Biol. 315, 325-37, 2002). All of the mentioned mutations or some of the mutations may be introduced into the β glucuronidase mutant. If glycine at position 368 in the amino acid sequence of *Escherichia coli* β glucuronidase is substituted with cysteine, this cysteine may form an SS bond with an antibody domain in some cases, and hence glycine at position 368 may be substituted not with cysteine but with serine to avoid this.

The positions of the above-mentioned amino acid mutations indicate positions in the amino acid sequence of β glucuronidase derived from *Escherichia coli*, and hence, in the case of the amino acid sequence of β glucuronidase derived from other organisms, no corresponding amino acid may be present in some cases at any of the above-mentioned positions. In such cases, alignment with the amino acid sequence of β glucuronidase derived from *Escherichia coli* is carried out on the basis of their amino acid sequence identity, and thereby the positions of amino acid mutations are specified. The amino acid sequence of wild-type β glucuronidase derived from *Escherichia coli* is set forth in SEQ ID NO: 1.

(2) Fusion Protein and Nucleic Acid

The fusion protein according to the present invention is characterized by containing: the β glucuronidase mutant according to the present invention; a linker peptide bound to the β glucuronidase mutant; and an antibody VH domain or VL domain bound to the linker peptide.

The linker peptide may be any linker peptide that allows the β glucuronidase mutant, VH domain, and VL domain to normally function. If the distance between the β glucuronidase mutant and the VH domain or VL domain is insufficient, the β glucuronidase mutant may fail to exhibit the activity in some cases, and hence the linker peptide needs a reasonable length. The length of the linker peptide depends on the types of the β glucuronidase mutant and antibody to be used, and is typically 10 to 60 angstroms, and preferably 30 to 40 angstroms. The number of amino acids of the linker peptide is needed to be a number of amino acids that give the mentioned length, typically 5 to 50, and preferably 15 to 20. The amino acid sequence of the linker peptide may be any of amino acid sequences of common linker peptides for use in production of fusion proteins. Specific examples thereof may include repetitive sequences of Gly-Gly-Gly-Gly-Ser ($G_4S$) (the number of repetitions is typically 2 to 5), repetitive sequences of Glu-Ala-Ala-Ala-Lys (EAAAK), and repetitive sequences of Asp-Asp-Ala-Lys-Lys (DDAKK).

The antibody VH domain or VL domain can be any antibody VH domain or VL domain selected according to an antigen targeted for detection, and is not limited to a particular antibody VH domain or VL domain. Specifically, an antibody VH domain or VL domain that specifically binds to an antigen targeted for detection, which will be described later, can be used. The scope of the antibody VH domain includes not only a VH domain of a common antibody (an antibody that binds to an antigen at its two domains: the VL domain and the VH domain) but also a VH domain of a heavy-chain antibody (e.g., a heavy-chain antibody derived from a camelid) (variable domain of heavy chain of heavy-chain antibody), that is, a VHH antibody.

The fusion protein according to the present invention may consist only of the three components of the β glucuronidase mutant, the linker peptide, and the VH domain or VL domain, and may contain other peptide, protein, or the like. Examples of such peptide or the like may include tag sequences for purification such as His-Tag, and tag sequences that solubilize expressed proteins such as a solubilizing tag sequence derived from thioredoxin and that derived from amyloid precursor protein.

While the β glucuronidase mutant, the linker peptide, and the VH domain or VL domain are disposed in this order in the fusion protein according to the present invention, the β glucuronidase mutant may be on the N-terminal side with the VH domain or VL domain being on the C-terminal side, and, reversely, the β glucuronidase mutant may be on the C-terminal side with the VH domain or VL domain being on the N-terminal side.

Although it is sufficient that one moiety of the β glucuronidase mutant be contained in the fusion protein, two moieties of the β glucuronidase mutant may be contained, and two or more moieties of the β glucuronidase mutant may be contained. If two moieties of the β glucuronidase mutant are contained, they are disposed to be adjacent to each other with a linker therebetween. The linker to be used in this case may be the same as the linker disposed between the β glucuronidase mutant and the VH domain or VL domain.

In addition to the above-described fusion protein, the present invention includes a nucleic acid encoding the fusion protein. Here, the "nucleic acid" refers primarily to deoxyribonucleic acid, but also includes ribonucleic acids and modified products of these nucleic acids.

(3) Method for Detecting Antigen

The method for detecting an antigen according to the present invention is characterized by a method for detecting an antigen in a sample, the method including the steps of: bringing the sample into contact with the fusion protein containing an antibody VH domain according to the present invention and the fusion protein containing an antibody VL domain according to the present invention; and detecting tetramer formation of the β glucuronidase mutant through change in enzyme activity. If the fusion protein according to the present invention is a fusion protein containing a heavy-chain antibody VH domain, the sample may be brought into contact only with this fusion protein containing a heavy-chain antibody VH domain. Further, when two fusion proteins each contain a single chain antibody in which a VH domain is linked to a VL domain via a linker (single chain variable fragment, scFv), the two fusion proteins may be brought into contact with a sample containing a multivalent antigen such as protein and bacterial cells to induce the enzyme activity through the binding of them.

This method utilizes the principle of an open sandwich method developed by the present inventors (H. Ueda et al., Nat. Biotechnol. 14, 1714-8, 1996), specifically, the principle that the interaction between a VH domain and a VL domain is enhanced by the presence of an antigen or the principle that the interaction between two VHHs is enhanced by the presence of an antigen, and the principle of the sandwich method using two antibody variable domains. In contrast to conventional antigen detection methods utilizing the open sandwich method (e.g., T. Yokozeki, H. Ueda, R. Arai, W. Mahoney and T. Nagamune. Anal. Chem. 74, 2500-4, 2002 and H. Ueda et al., J. Immunol. Methods 279, 209-18, 2003), in which an N-terminus-deleted mutant and a C-terminus-deleted mutant are used, detection of an antigen is carried out by using a β glucuronidase mutant in the present invention. The detection principle will be described in the following. β glucuronidase comes to exhibit the activity through formation of a tetramer. The β glucuronidase mutant according to the present invention forms a dimer but does not form a tetramer in normal condition because a mutation that lowers the intermonomer affinity of some parts has been introduced thereinto. If no antigen is present in a sample, the interaction between the VH domain and the VL domain remains weak, and hence a dimer of the β glucuronidase mutant linked to the VH domain and that linked to the VL domain also remains as it is and scarcely forms a tetramer. If an antigen is present in a sample, in contrast, the interaction between the VH domain and the VL domain is enhanced, and this interaction allows a dimer of the β glucuronidase mutant linked to the VH domain and that linked to the VL domain to bind together to form a tetramer, which in turn exhibits activity. Therefore, whether an antigen is present in a sample can be determined by measuring the β glucuronidase activity.

The antigen targeted for detection is not limited, and a small molecule compound (e.g., a compound with a molecular weight of 1000 or lower) may be targeted for detection, and a macromolecule such as a protein may be targeted for detection. Since the method according to the present invention can be applied to diagnosis of diseases, toxicity test for foods, environmental analysis, and so on, it is preferable to target substances relating to them for detection. Specific examples thereof include neonicotinoid agrochemicals such as imidacloprid; environmental pollutants such as polychlorinated biphenyl and bisphenol A; toxic substances such as mycotoxin; biological matters such as osteocalcin (effective for diagnosis of osteoporosis), corticoid, estradiol, aldosterone, and lysozyme (such as hen egg white lysozyme); and drugs such as digoxin.

The sample may be any sample suspected to contain an antigen targeted for detection, and examples thereof include a collected sample from a human (blood, saliva, urine, etc.), water or soil suspected to be polluted, and a food or a raw material of a food.

Although the method for bringing the sample into contact with the fusion protein is not limited, contact is achieved in typical cases by allowing the sample and the fusion protein to coexist in a solution. Alternatively, the sample may be allowed to coexist not with the fusion protein itself but with cells that express the fusion protein. The conditions for this contact step, including the temperature, the time, the pH of the solution, and the amount of usage of the fusion protein, may be those commonly used for β glucuronidase; for example, the temperature in the contact step is preferably about 20 to 37° C., the time to keep contact is preferably about 10 to 60 minutes, the pH of the solution is preferably about 6.8 to 7.5, and the concentration of the fusion protein in the solution is preferably about 10 to 100 nM.

Tetramer formation of the β glucuronidase mutant can be detected through change (increase or development) in the activity of the β glucuronidase mutant contained in the fusion protein. The activity of the β glucuronidase mutant contained in the fusion protein can be measured by using an activity measurement method commonly used for β glucuronidase. For example, the activity can be measured by adding a chromogenic substrate or fluorescent substrate for β glucuronidase and quantifying a substance generated from the substrate. Examples of the chromogenic substance for β glucuronidase include X-Gluc, 4-nitrophenyl α-glucopyranoside, and 4-nitrophenyl β-D-glucuronide; examples of the fluorescent substance for β glucuronidase include 4-methylumbelliphenyl-β-D-glucuronide, fluorescein di-β-D-glucuronide, fluorescein di-β-D-glucuronide, and dimethyl ester. Quantification of a substance generated from such a substrate can be carried out by measuring absorbance, fluorescence intensity, and so on at a particular wavelength. If the substrate is 4-nitrophenyl β-D-glucuronide, for example, the product can be quantified through measurement of the absorbance around 405 nm; if the substrate is 4-methylumbelliphenyl-β-D-glucuronide, the product can be quantified through excitation with fluorescence at 340 nm followed by measurement of the fluorescence intensity around 480 nm.

(4) Antigen Detection Kit

The antigen detection kit according to the present invention is characterized by including the fusion protein containing an antibody VH domain according to the present invention and the fusion protein containing an antibody VL domain according to the present invention. If the fusion protein according to the present invention is a fusion protein containing a heavy-chain antibody VH domain, however, only this fusion protein containing a heavy-chain antibody VH domain may be included in the kit. This kit can detect an antigen in a sample on the basis of the above-described principle of antigen detection.

The kit may include a component other than the fusion protein containing an antibody VH domain according to the present invention and the fusion protein containing an antibody VL domain according to the present invention. For example, since a substrate is needed for measurement of enzyme activity, the kit may include such a substrate. In addition, the kit may include, for example, a reagent or instrument to quantify a substance generated from the substrate or a substance to stabilize the fusion proteins or the substrate.

EXAMPLES

Hereinafter, the present invention will be described in more detail; however, the present invention is not limited to Examples.

[Example 1] Construction of Expression Vector Encoding GUS(IV-5)KE

IV-5 (N27Y, F51Y, A64V, D185N, I349F, G368C, N369S, Y517F, Y525F, G559S, K567R, F582Y, Q585H, G601D) described in H. Flores and A. D. Ellington, J. Mol. Biol., 315, 325-37, 2002 was selected as an *Escherichia coli* β glucuronidase mutant having high thermal stability and retaining the activity more than the wild type, and, by providing the gene therefor with three mutations, a DNA was artificially synthesized (Eurofins Genomics K.K., Tokyo, Japan), the three mutations being C368S to avoid the possibility of SS bond formation with an antibody domain, and M516K and F517E to reduce the interdimer interaction (the sequence of this DNA is set forth in SEQ ID NO: 2; the amino acid sequence of the protein encoded by the DNA is set forth in SEQ ID NO: 3). This DNA encoded in a plasmid was amplified by PCR with reaction at 94° C. for 2 minutes followed by 30 cycles of reaction at 94° C. for 30 seconds, at 55° C. for 30 seconds, and at 68° C. for 1 minute by using the primers GUS_NotBack (ATAAGAATGCGGCCGC-TATGTTACGTCCTGTAGAAA) (SEQ ID NO: 4) and GUSmIV5 XhoFor (GCCCTCGAGTCAT-TGTTTGTCTCCCTG) (SEQ ID NO: 5) and KOD-Plus-Neo DNA polymerase (TOYOBO CO., LTD.). The amplified GUS(IV-5)KE fragment was cleaved with the restriction enzymes NotI and XhoI (New England Biolabs Japan, Tokyo), and inserted through ligation into the GUSm moiety of each of pET32-VH(NP)-GUSm and pET32-VL(NP)-GUSm (Su et al., Analyst, 143, 2096-101, 2018) cleaved with the same two restriction enzymes, and their sequences were confirmed.

[Example 2] Expression and Purification of Fusion Protein

*Escherichia coli* SHuffle T7 lysY was transformed by using pET32-VH(NP)-GUS(IV-5)KE and pET32-VL(NP)-GUS(IV-5)KE. Thereafter, *Escherichia coli* retaining the plasmid was cultured with 500 mL of LBA medium (10 g/L triptone, 5 g/L yeast, 5 g/L NaCl, 100 μg/mL ampicillin) at 30° C. until the $OD_{600}$ reached 0.6, 0.5 mM IPTG was then added thereto, and the *Escherichia coli* was further cultured at 16° C. for 16 hours. After collecting the bacterial cells by centrifugation, the *Escherichia coli* was suspended in 40 mL of Extraction buffer (50 mM sodium phosphate, 300 mM sodium chloride, pH 7.0) and disrupted with a cell disrupter (Constant Systems Limited, UK) to prepare a bacterial cell lysate. Centrifugation was performed at 1000 g for 20 minutes, and the supernatant was collected and purified by immobilized metal affinity chromatography. Specifically, an appropriate amount of Talon metal affinity gel (Takara Bio Inc., Clontech Laboratories, Inc.) was added to the supernatant, and the resultant was stirred for 2 hours, then transferred into a Talon disposable column and washed three times with 10 mL of Extraction buffer, and the protein bound to the gel was eluted by using Extraction buffer containing 2.5 mL of 150 mM imidazole. The purified thioredoxin (Trx) fusion proteins were analyzed through SDS-PAGE.

[Example 3] Evaluation of Antigen Dependence of GUS Activity

Purified Trx-VH(NP)-GUS(IV-5)KE and Trx-VL(NP)-GUS(IV-5)KE were subjected to buffer exchange with PBST (10 mM phosphate, 137 mM NaCl, 2.7 mM KCl, 0.05% Tween 20; pH 7.4), and preparation was carried out in a black half-well microplate (675077, Greiner Bio-One International GmbH) so that the final concentrations each reached 0.1 μM (n=3). Thereto, the antigen NP (4-hydroxy-3-nitrophenyl acetyl) or PBST was added to reach a final concentration of 0.1 μM, incubation was performed at 25° C. for 5 minutes, 0.3 mg $mL^{-1}$ 4-methylumbelliphenyl-β-D-glucuronide (MUG, Wako Pure Chemical Industries, Ltd.) as a fluorescent substrate was then added thereto to a total volume of 100 μL, and the fluorescence intensity of each well was measured (excitation: 340 nm, fluorescence: 480 nm) at intervals of 2 minutes. FIG. 1 shows the results. When Trx-VH(NP)-GUS(IV-5)KE and Trx-VL(NP)-GUS(IV-5)KE were contained but NP was not added, almost no change in absorbance was found after 26 minutes; when NP was added, on the other hand, slight increase in absorbance, that is, in GUS activity was found. Although the increase level was lower than an expected value, the background activity, which was a problem inherent in conventional GUSm systems, was markedly reduced. Further, examination using the protein stored at 4° C. overnight was made on the dependence of fluorescence 14 minutes after the beginning of reaction on the concentration of the antigen NP and that on the concentration of 5-iodo-NP (NIP), an analog of NP with an association constant 10 times higher than that of NP, and revealed that, although the difference was small, the activity exhibits antigen dependence. From the fact that conventional GUSm (M516K, Y517E mutant) was decomposed during storage under such conditions, it was suggested that GUS(IV-5)KE has higher storage stability.

[Example 4] Construction of Mutant with Mutated Interdimer Interface Residues and Activity Measurement GUS(IV-5)KE was highly stable, but had a problem of small activity increase in tetramer formation. To overcome this, screening was carried out for a mutant that exhibits larger activity increase through mutation of the amino acids at the relating sites. Specifically, one or both of the interface residues KE of pET32-VL(NP)-GUS(IV-5) was/were returned to those of wild type by site-specific mutation using overlap PCR to construct ME, KY, and MY. Then, proteins were prepared with the same method as in Example 2.

Figure 2:
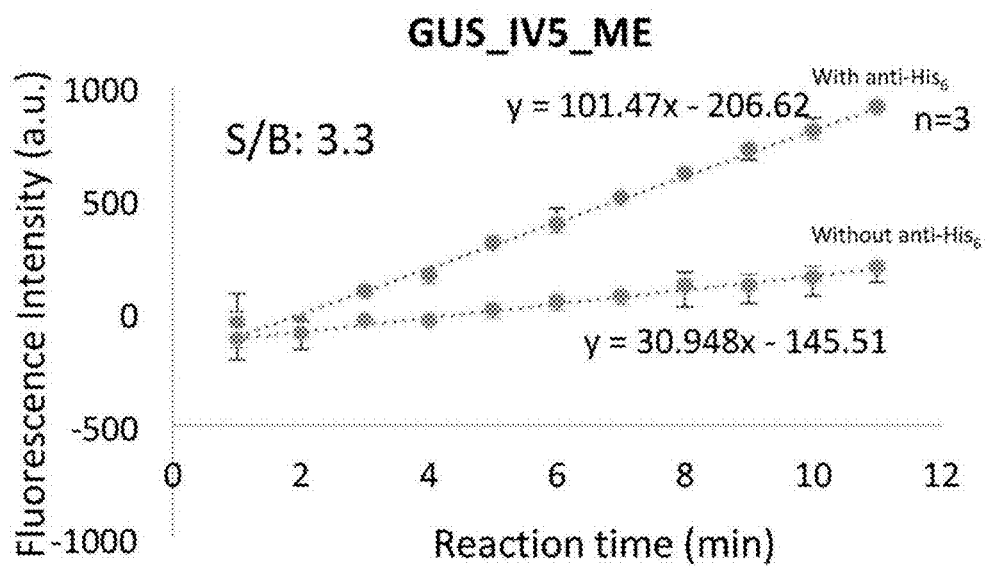
FIG. 2 shows a graph representing the activity of GUS (IV-5)ME in the presence and absence of an anti-His$_6$ antibody (N=3).
Figure 3:
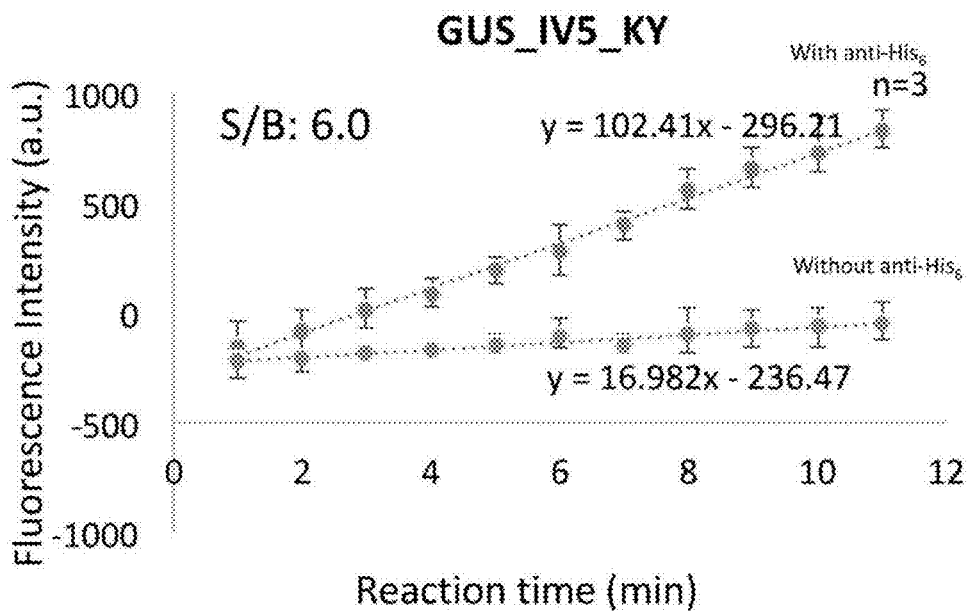
FIG. 3 shows a graph representing the activity of GUS (IV-5)KY in the presence and absence of an anti-His$_6$ antibody (N=3).
Figure 4:
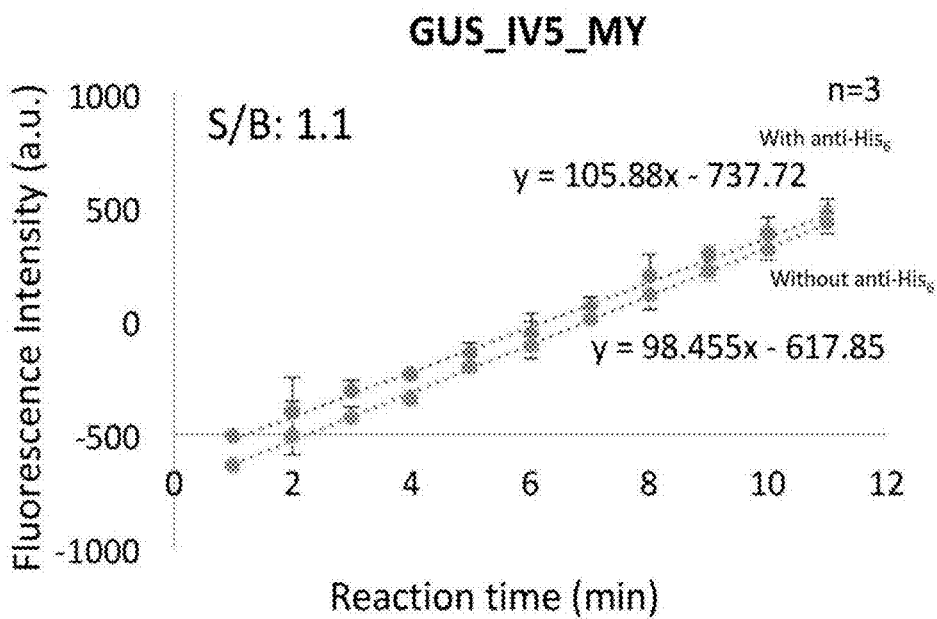
FIG. 4 shows a graph representing the activity of GUS (IV-5)MY in the presence and absence of an anti-His$_6$ antibody (N=3).
Figure 5:
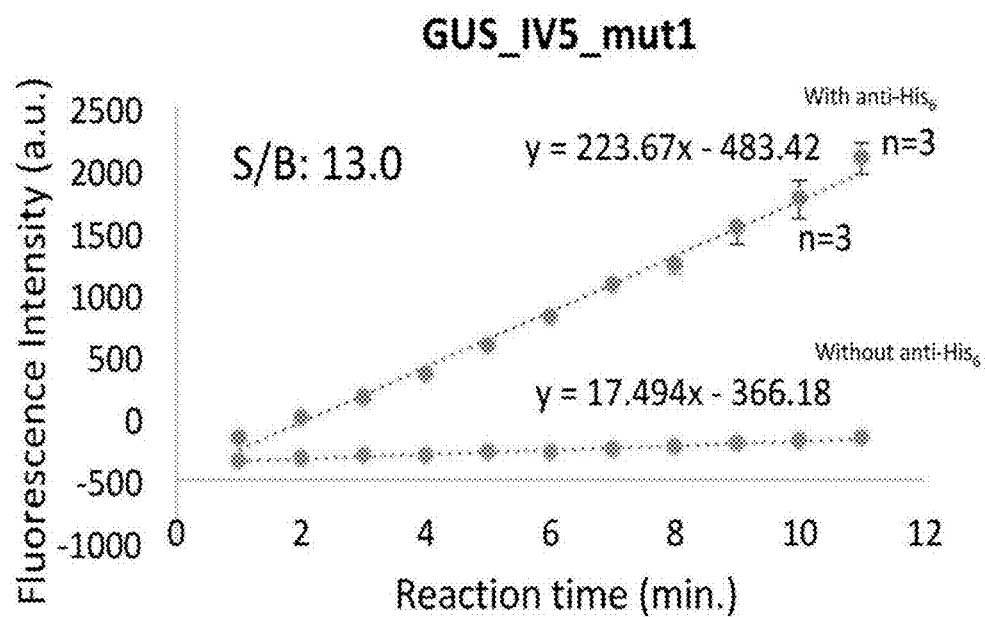
FIG. 5 shows a graph representing the activity of GUS (IV-5)KW in the presence and absence of an anti-His$_6$ antibody (N=3).
Figure 6:
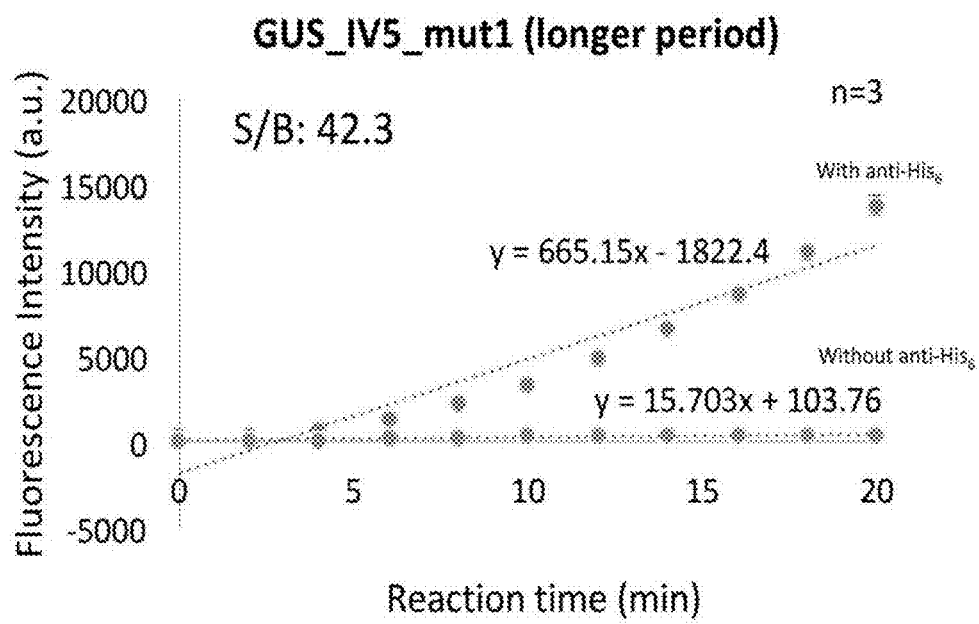
FIG. 6 shows a graph representing the activity of GUS (IV-5)KW in the presence and absence of an anti-His$_6$ antibody (N=3).

For tetramerization of the proteins, a His6 tag, being present in the linker domain between Trx and VL(NP), was used in place of the antigen; the proteins were each reacted with an equal amount of moles of a PentaHis antibody (QIAGEN) or anti-$His_6$ antibody (9C11, Wako Pure Chemical Industries, Ltd.), a fluorescent substrate was then added thereto, and activity (temporal variation of fluorescence every 1 minute) measurement was carried out. As can be seen from the results shown in FIGS. 2 to 4, a high S/B ratio (the ratio between activities with and without the antibody, 6.0) was successfully obtained especially for the KY mutant, and a very low S/B ratio was obtained for the wild-type sequence MY, as expected. From this, Lys at position 516 was determined to be important for activity control, and a KW mutant with Lys left at position 516 and the residue at position 517 changed to an aromatic analogous thereto, Trp, was constructed. This mutant protein was prepared in the above-described manner, and activity measurement was carried out on the basis of the presence or absence of the PentaHis antibody, finding that the KW mutant exhibited very high values: the average S/B ratio in 11 minutes after the beginning of reaction being 13.0 (FIG. 5) and that in 20 minutes after the beginning of reaction being 42.3 (FIG. 6). Moreover, the fluorescence intensity 11 minutes after the beginning of reaction with addition of the antibody was significantly higher than those of GUS(IV-5)MY and GUS-KE (FIG. 5), and a value further increased by three times or more was exhibited 20 minutes after the beginning of reaction (FIG. 6).

[Example 5] Characterization of KW Mutant

Figure 7:
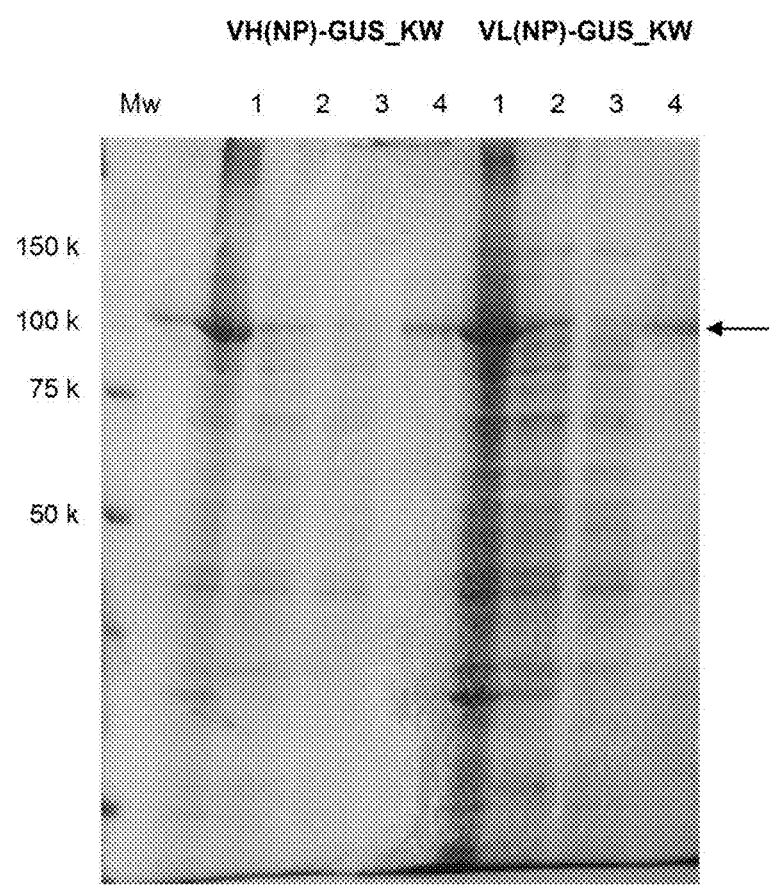
FIG. 7 shows an electropherogram of VH/VL(NP)-GUS (IV-5)KW. Lane 1: precipitate of bacterial cell lysate, lane 2: supernatant of bacterial cell lysate, lane 3: unbound fraction of Talon metal affinity gel, lane 4: bound fraction of Talon metal affinity gel. The arrow in the figure indicates VH(NP) GUS(IV-5)KW or VL (NP) GUS (IV-5) KW.
Figure 8:
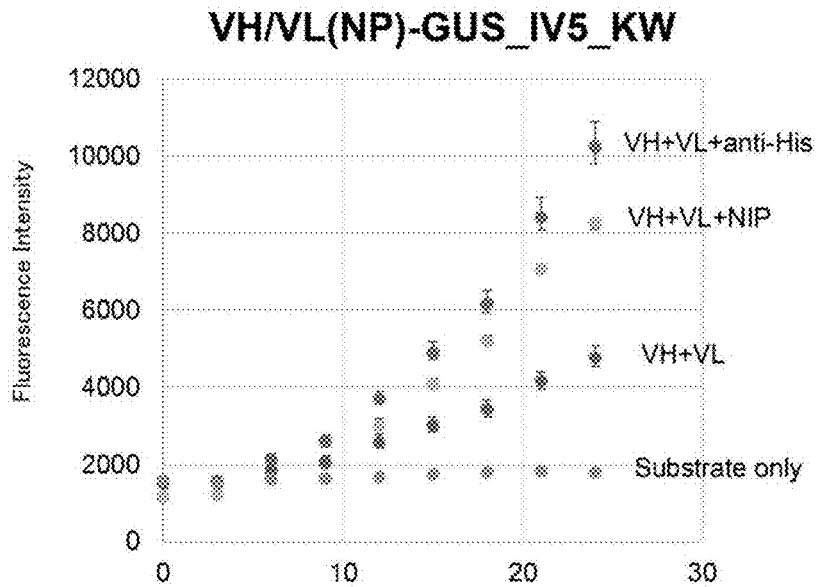
FIG. 8 shows a graph representing the activity of VH/VL (NP)-GUS(IV-5)KW in the presence and absence of an anti-His$_6$ antibody or NIP.
Figure 9:
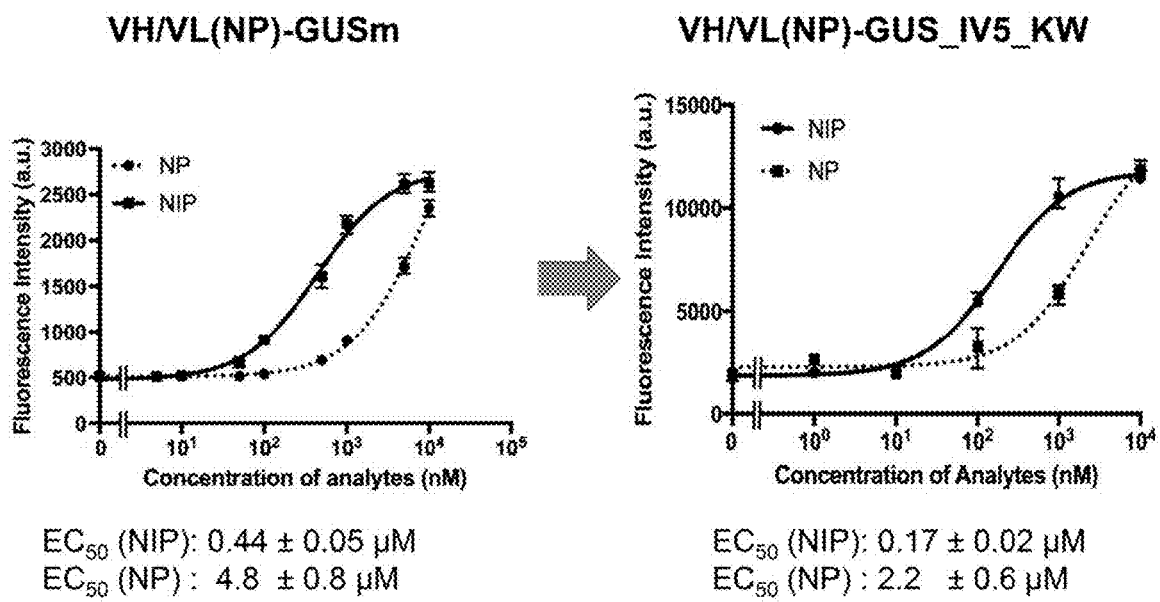
FIG. 9 shows graphs representing the relationship between fluorescence intensity and antigen concentrations in VH/VL(NP)-GUSm (left) or VH/VL(NP)-GUS(IV-5)KW (right).

High-performance GUS(IV-5)KW revealed in Example 4 was additionally constructed as that of VH(NP)-fused type, and expression and purification thereof was carried out with the same method as in Example 2, successfully providing it with a sufficient degree of purification in SDS-PAGE (FIG. 7). The two products were mixed, to which the antigen NIP or the anti-$His_6$ antibody was added, and the temporal variation of fluorescence intensity after addition of MUG was measured to find a significantly higher signal than in the case with neither the antigen nor the antibody (FIG. 8). Then, fluorescence intensity (GUS activity) 18 minutes after addition of MUG was measured with addition of different concentrations of the antigen NP or NIP (FIG. 9). The system using GUS(IV-5)KW allowed antigen detection with sensitivity and signal intensity higher than those achieved by conventional systems using GUSm.

Further, for evaluation of thermal stability, 0.1 μM Trx-VH(NP)-GUS (IV-5)KW or $His_6$-GUS (IV-5)KW was incubated in PBST at different temperatures ranging from 25° C. to 80° C. for 10 minutes, and the activity in the presence or absence of the anti-His antibody was measured on the basis of fluorescence in the above-described manner. The results showed that, even in the case with treatment at 50° C. for 10 minutes, Trx-VH(NP)-GUS(IV-5)KW and $His_6$-GUS(IV-5)KW respectively kept 46.2% and 59.7% of activity to a sample treated at 25° C. for 10 minutes with addition of the antibody. In contrast to this, the activity of VH-GUS(KE) after treatment at 50° C. was only 0.29% under the same conditions. Further, the activity in the absence of the antibody was observed to be 49.0% of that in the presence of the antibody in the case of 25° C., and, similarly, 65.6% in the case of 37° C., which again suggested that the structural change associated with the decomposition of GUS leads to background activity.

[Example 6] Measurement of Caffeine Concentration Using $V_HH$

To apply the thermally stabilized high-performance mutant GUS(IV-5)KW to caffeine detection using a nanobody (Sonneson, G. J. and Horn, J. R., Biochemistry, 48, 6693-5, 2009), which is known to form a dimer in the presence of the antigen caffeine, a synthetic gene for the variable domain VHH(Caf) of an anti-caffeine nanobody having the restriction enzyme sites NcoI and HindIII at the ends (Eurofins Japan) (SEQ ID NO: 6) was inserted into the upstream of the GUS(IV-5)KW gene by using the restriction enzymes NcoI/HindIII to construct a Trx-VHH(Caf)-GUS (IV-5)KW fusion protein expression vector.

Figure 10:
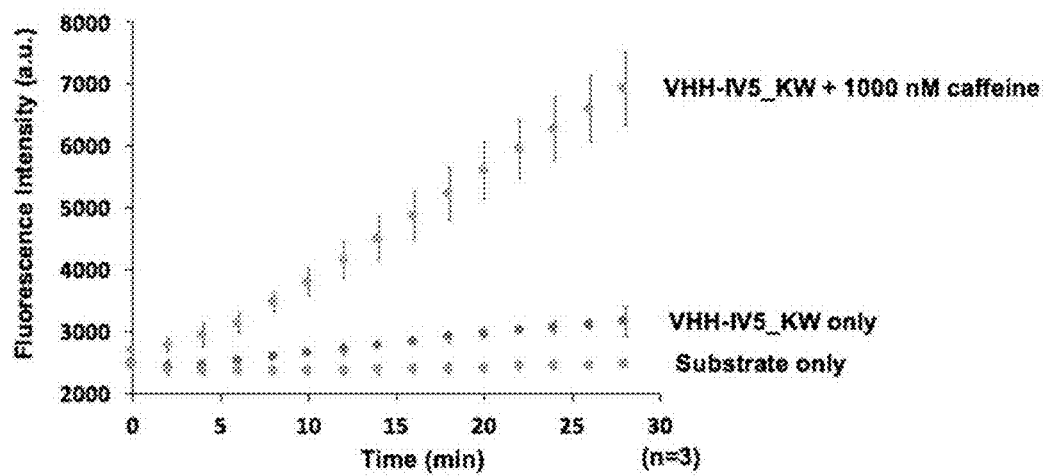
FIG. 10 shows a graph representing the activity of VHH (Caf)-GUS(IV-5)KW in the presence and absence of caffeine.
Figure 11:
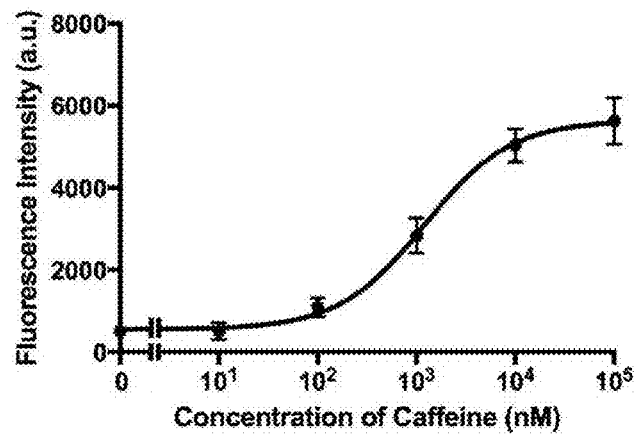
FIG. 11 shows a graph representing the relationship between fluorescence intensity and caffeine concentrations in VHH(Caf)-GUS(IV-5)KW.

A protein was prepared by using the vector with the same method as in Example 2, and the antigen dependence of GUS activity was evaluated with the same method as in Example 3. Because high-performance GUS(IV-5)KW was used as a reporter enzyme, reduced background activity and an increased S/B ratio were provided (FIG. 10). Further, the fusion protein in 0.1 µM was mixed with 0 to 10 µM caffeine, and the antigen concentration dependence was measured. The fluorescence substrate 4-methylumbelliphenyl-β-D-glucuronide was added at a final concentration of 0.3 mg mL-1, and fluorescence intensity 20 minutes thereafter was measured (excitation wavelength: 340 nm, fluorescence wavelength: 480 nm) to reveal remarkable caffeine concentration dependence of GUS activity (FIG. 11). Through curve fitting, $EC_{50}$ was calculated to be 1.2±0.1 µM, and LOD to be 40 nM. This sensitivity was enough to allow measurement of caffeine concentrations of beverages (tea: 140 µM, coffee: 5 mM) (Lisko, J. G., et al., Nicotine Tob. Res., 19, 484-92, 2017).

[Example 7] Measurement of Specific Activity of GUS(IV-5)KW Enzyme

Figure 12:
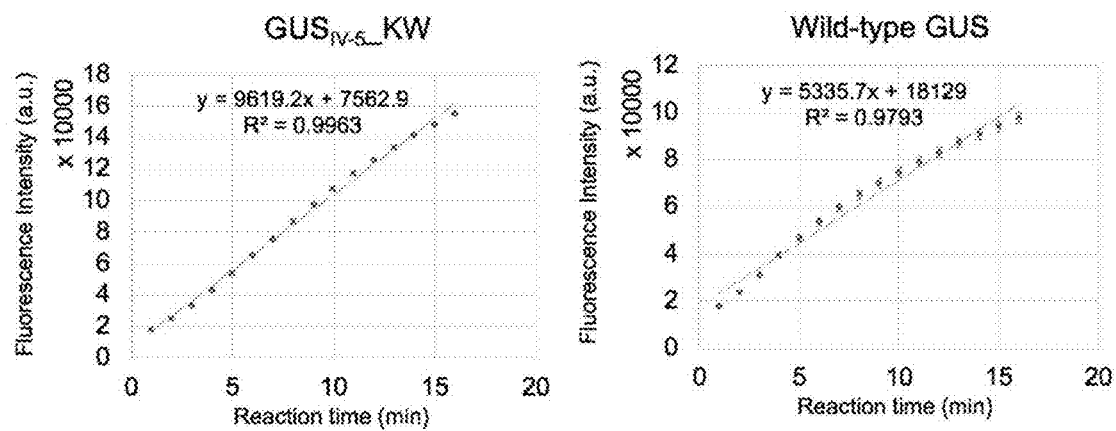
FIG. 12 shows graphs representing the specific activities, kcat, of GUS(IV-5)KW (left) and wild-type GUS (right).

To evaluate the specific activity of the mutant GUS(IV-5)KW, the specific activity (turnover number), $k_{cat}$, of Trx-VL(NP)-GUS(IV-5)KW protein formed through tetramerization by addition of a PentaHis antibody (QIAGEN), which recognizes a His-tag, was measured, and compared with that of wild-type GUS. The anti-PentaHis antibody in a ½ amount of moles was mixed with 4.75 µg/mL Trx-VL(NP)-GUS(IV-5)KW, 0.3 mg/mL 4-methyl-umbelliphenyl-β-D-glucuronide as a substrate was then added thereto, and fluorescence intensity was measured every 1 minute for 15 minutes (FIG. 12, left). The inclination of the graph was calculated to find that $k_{cat}$ of tetramerized GUS(IV-5)KW was 1.25 s$^{-1}$. On the other hand, measurement of the activity of wild-type GUS (2.88 µg/mL) was carried out with the same method using Trx-VL(NP)-GUS protein (FIG. 12, right), and $k_{cat}$ of wild-type GUS was calculated to be 1.19 s$^{-1}$. Thus, the mutant GUS(IV-5)KW exhibited $k_{cat}$ similar to or higher than that of wild-type GUS.

All of the publications, patents, and patent applications cited herein are directly incorporated herein by reference.

INDUSTRIAL APPLICABILITY

The present invention is useful for diagnosis of diseases, food inspection, environmental analysis, and so on, and hence applicable in industrial fields relating to them.

Sequence Listing

---

The invention claimed is:

1. A mutant of β glucuronidase, wherein, in an amino acid sequence of *Escherichia coli* β glucuronidase, methionine at position 516 is substituted with lysine, and tyrosine at position 517 is substituted with a tryptophan, and, in the amino acid sequence of *Escherichia coli* β glucuronidase, asparagine at position 27 is substituted with tyrosine, phenylalanine at position 51 is substituted with tyrosine, alanine at position 64 is substituted with valine, aspartic acid at position 185 is substituted with asparagine, isoleucine at position 349 is substituted with phenylalanine, glycine at position 368 is substituted with cysteine, asparagine at position 369 is substituted with serine, tyrosine at position 525 is substituted with phenylalanine, glycine at position 559 is substituted with serine, lysine at position 567 is substituted with arginine, phenylalanine at position 582 is substituted with tyrosine, glutamine at position 585 is substituted with histidine, and glycine at position 601 is substituted with aspartic acid.

2. The β glucuronidase mutant according to claim 1, wherein, in the amino acid sequence of *Escherichia coli* β glucuronidase, cysteine at position 368 is substituted with serine.

3. A fusion protein comprising: the β glucuronidase mutant according to claim 1; a linker peptide bound to the β glucuronidase mutant; and an antibody VH domain or VL domain bound to the linker peptide.

4. A nucleic acid encoding the fusion protein according to claim 3.

5. A method for detecting an antigen in a sample, comprising:
bringing the sample into contact with the fusion protein comprising an antibody VH domain according to claim 3 and the fusion protein comprising an antibody VL domain according to claim 3; and detecting tetramer formation of the b-glucuronidase mutant through change in enzyme activity.

6. An antigen detection kit comprising the fusion protein comprising an antibody VH domain according to claim 3 and the fusion protein comprising an antibody VL domain according to claim 3.

7. A fusion protein comprising: the β glucuronidase mutant according to claim 1; a linker peptide bound to the β glucuronidase mutant; and a heavy-chain antibody VH domain bound to the linker peptide.

8. A nucleic acid encoding the fusion protein according to claim 7.

9. A method for detecting an antigen in a sample, comprising: bringing the sample into contact with the fusion protein according to claim 7; and detecting tetramer formation of the b-glucuronidase mutant through change in enzyme activity.

10. An antigen detection kit comprising the fusion protein according to claim 7.

11. A fusion protein comprising: a β glucuronidase mutant; a linker peptide bound to the β glucuronidase mutant; and an antibody VH domain or VL domain bound to the linker peptide, wherein the β glucuronidase mutant is a β glucuronidase mutant, wherein 1) in the amino acid sequence of *Escherichia coli* β glucuronidase, methionine at position 516 is substituted with lysine, and tyrosine at position 517 is substituted with tryptophan, and 2) in the amino acid sequence of *Escherichia coli* β glucuronidase, asparagine at position 27 is substituted with tyrosine, phenylalanine at position 51 is substituted with tyrosine, alanine at position 64 is substituted with valine, aspartic acid at position 185 is substituted with asparagine, isoleucine at position 349 is substituted with phenylalanine, glycine at position 368 is substituted with serine, asparagine at position 369 is substituted with serine, tyrosine at position 525 is substituted with phenylalanine, glycine at position 559 is substituted with serine, lysine at position 567 is substituted with arginine, phenylalanine at position 582 is substituted with tyrosine, glutamine at position 585 is substituted with histidine, and glycine at position 601 is substituted with aspartic acid.

12. A nucleic acid encoding the fusion protein according to claim 11.

13. A method for detecting an antigen in a sample, comprising: bringing the sample into contact with the fusion protein comprising an antibody VH domain according to claim 11 and the fusion protein comprising an antibody VL domain according to claim 11; and detecting tetramer formation of the b-glucuronidase mutant through change in enzyme activity.

14. An antigen detection kit comprising the fusion protein comprising an antibody VH domain according to claim 11 and the fusion protein comprising an antibody VL domain according to claim 11.

15. A fusion protein comprising: a β glucuronidase mutant; a linker peptide bound to the β glucuronidase mutant; and a heavy-chain antibody VH domain bound to the linker peptide, wherein the β glucuronidase mutant is a β glucuronidase mutant, wherein 1) in the amino acid sequence of *Escherichia coli* β glucuronidase, methionine at position 516 is substituted with lysine, and tyrosine at position 517 is substituted with tryptophan, and 2) in the amino acid sequence of *Escherichia coli* β glucuronidase, asparagine at position 27 is substituted with tyrosine, phenylalanine at position 51 is substituted with tyrosine, alanine at position 64 is substituted with valine, aspartic acid at position 185 is substituted with asparagine, isoleucine at position 349 is substituted with phenylalanine, glycine at position 368 is substituted with serine, asparagine at position 369 is substituted with serine, tyrosine at position 525 is substituted with phenylalanine, glycine at position 559 is substituted with serine, lysine at position 567 is substituted with arginine, phenylalanine at position 582 is substituted with tyrosine, glutamine at position 585 is substituted with histidine, and glycine at position 601 is substituted with aspartic acid.

16. A nucleic acid encoding the fusion protein according to claim 15.

17. A method for detecting an antigen in a sample, comprising: bringing the sample into contact with the fusion protein according to claim 15; and detecting tetramer formation of the b-glucuronidase mutant through change in enzyme activity.

18. An antigen detection kit comprising the fusion protein according to claim 15.

* * * * *

SEQUENCE LISTING

```
<160> NUMBER OF SEQ ID NOS: 6

<210> SEQ ID NO 1
<211> LENGTH: 603
<212> TYPE: PRT
<213> ORGANISM: Escherichia coli

<400> SEQUENCE: 1

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140
```

```
Pro Gly Met Val Ile Thr Asp Glu Asn Gly Lys Lys Gln Ser Tyr
145                 150                 155                 160

Phe His Asp Phe Phe Asn Tyr Ala Gly Ile His Arg Ser Val Met Leu
            165                 170                 175

Tyr Thr Thr Pro Asn Thr Trp Val Asp Asp Ile Thr Val Thr His
                180                 185                 190

Val Ala Gln Asp Cys Asn His Ala Ser Val Asp Trp Gln Val Ala
            195                 200                 205

Asn Gly Asp Val Ser Val Glu Leu Arg Asp Ala Asp Gln Gln Val Val
        210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
                260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
            355                 360                 365

Asn Lys Pro Lys Glu Leu Tyr Ser Glu Glu Ala Val Asn Gly Glu Thr
370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
                420                 425                 430

Arg Lys Leu Asp Pro Thr Arg Pro Ile Thr Cys Val Asn Val Met Phe
            435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Thr Glu Tyr Gly Val Asp Thr Leu Ala Gly
                500                 505                 510

Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
            530                 535                 540

Gly Glu Gln Val Trp Asn Phe Ala Asp Phe Ala Thr Ser Gln Gly Ile
545                 550                 555                 560
```

```
Leu Arg Val Gly Gly Asn Lys Lys Gly Ile Phe Thr Arg Asp Arg Lys
            565                 570                 575

Pro Lys Ser Ala Ala Phe Leu Leu Gln Lys Arg Trp Thr Gly Met Asn
        580                 585                 590

Phe Gly Glu Lys Pro Gln Gln Gly Gly Lys Gln
    595                 600

<210> SEQ ID NO 2
<211> LENGTH: 1809
<212> TYPE: DNA
<213> ORGANISM: Escherichia coli
<220> FEATURE:
<221> NAME/KEY: CDS
<222> LOCATION: (1)..(1809)

<400> SEQUENCE: 2 atg tta cgt cct gta gaa acc cca acc cgt gaa atc aaa aaa ctc gac      48
Met Leu Arg Pro Val Glu Thr Pro Thr Arg Glu Ile Lys Lys Leu Asp
  1               5                  10                  15 ggc ctg tgg gca ttc agt ctg gat cgc gaa tac tgt gga att gat cag      96
Gly Leu Trp Ala Phe Ser Leu Asp Arg Glu Tyr Cys Gly Ile Asp Gln
                 20                  25                  30 cgt tgg tgg gaa agc gcg tta caa gaa agc cgg gca att gct gtg cca     144
Arg Trp Trp Glu Ser Ala Leu Gln Glu Ser Arg Ala Ile Ala Val Pro
             35                  40                  45 ggc agt tat aac gat cag ttc gcc gat gca gat att cgt aat tat gtg     192
Gly Ser Tyr Asn Asp Gln Phe Ala Asp Ala Asp Ile Arg Asn Tyr Val
         50                  55                  60 ggc aac gtc tgg tat cag cgc gaa gtc ttt ata ccg aaa ggt tgg gca     240
Gly Asn Val Trp Tyr Gln Arg Glu Val Phe Ile Pro Lys Gly Trp Ala
 65                  70                  75                  80 ggc cag cgt atc gtg ctg cgt ttc gat gcg gtc act cat tac ggc aaa     288
Gly Gln Arg Ile Val Leu Arg Phe Asp Ala Val Thr His Tyr Gly Lys
                 85                  90                  95 gtg tgg gtc aat aat cag gaa gtg atg gag cat cag ggc ggc tat acg     336
Val Trp Val Asn Asn Gln Glu Val Met Glu His Gln Gly Gly Tyr Thr
            100                 105                 110 cca ttt gaa gcc gat gtc acg ccg tat gtt att gcc ggg aaa agt gta     384
Pro Phe Glu Ala Asp Val Thr Pro Tyr Val Ile Ala Gly Lys Ser Val
        115                 120                 125 cgt atc acc gtt tgt gtg aac aac gaa ctg aac tgg cag act atc ccg     432
Arg Ile Thr Val Cys Val Asn Asn Glu Leu Asn Trp Gln Thr Ile Pro
    130                 135                 140 ccg gga atg gtg att acc gac gaa aac ggc aag aaa aag cag tct tac     480
Pro Gly Met Val Ile Thr Asp Glu Asn Gly Lys Lys Lys Gln Ser Tyr
145                 150                 155                 160 ttc cat gat ttc ttt aac tat gcc ggg atc cat cgc agc gta atg ctc     528
Phe His Asp Phe Phe Asn Tyr Ala Gly Ile His Arg Ser Val Met Leu
                165                 170                 175 tac acc acg ccg aac acc tgg gtg aac gat atc acc gtg gtg acg cat     576
Tyr Thr Thr Pro Asn Thr Trp Val Asn Asp Ile Thr Val Val Thr His
            180                 185                 190 gtc gcg caa gac tgt aac cac gcg tct gtt gac tgg cag gtg gtg gcc     624
Val Ala Gln Asp Cys Asn His Ala Ser Val Asp Trp Gln Val Val Ala
        195                 200                 205 aat ggt gat gtc agc gtt gaa ctg cgt gat gcg gat caa cag gtg gtt     672
Asn Gly Asp Val Ser Val Glu Leu Arg Asp Ala Asp Gln Gln Val Val
    210                 215                 220 gca act gga caa ggc act agc ggg act ttg caa gtg gtg aat ccg cac     720
Ala Thr Gly Gln Gly Thr Ser Gly Thr Leu Gln Val Val Asn Pro His
225                 230                 235                 240
```

-continued

| | | |
|---|---|---|
| ctc tgg caa ccg ggt gaa ggt tat ctc tat gaa ctg tgc gtc aca gcc<br>Leu Trp Gln Pro Gly Glu Gly Tyr Leu Tyr Glu Leu Cys Val Thr Ala<br>245 250 255 | 768 |
| aaa agc cag aca gag tgt gat atc tac ccg ctt cgc gtc ggc atc cgg<br>Lys Ser Gln Thr Glu Cys Asp Ile Tyr Pro Leu Arg Val Gly Ile Arg<br>260 265 270 | 816 |
| tca gtg gca gtg aag ggc gaa cag ttc ctg att aac cac aaa ccg ttc<br>Ser Val Ala Val Lys Gly Glu Gln Phe Leu Ile Asn His Lys Pro Phe<br>275 280 285 | 864 |
| tac ttt act ggc ttt ggt cgt cat gaa gat gcg gac ttg cgt ggc aaa<br>Tyr Phe Thr Gly Phe Gly Arg His Glu Asp Ala Asp Leu Arg Gly Lys<br>290 295 300 | 912 |
| gga ttc gat aac gtg ctg atg gtg cac gac cac gca tta atg gac tgg<br>Gly Phe Asp Asn Val Leu Met Val His Asp His Ala Leu Met Asp Trp<br>305 310 315 320 | 960 |
| att ggg gcc aac tcc tac cgt acc tcg cat tac cct tac gct gaa gag<br>Ile Gly Ala Asn Ser Tyr Arg Thr Ser His Tyr Pro Tyr Ala Glu Glu<br>325 330 335 | 1008 |
| atg ctc gac tgg gca gat gaa cat ggc atc gtg gtg ttt gat gaa act<br>Met Leu Asp Trp Ala Asp Glu His Gly Ile Val Val Phe Asp Glu Thr<br>340 345 350 | 1056 |
| gct gct gtc ggc ttt aac ctc tct tta ggc att ggt ttc gaa gcg agc<br>Ala Ala Val Gly Phe Asn Leu Ser Leu Gly Ile Gly Phe Glu Ala Ser<br>355 360 365 | 1104 |
| agc aag ccg aaa gaa ctg tac agc gaa gag gca gtc aac ggg gaa act<br>Ser Lys Pro Lys Glu Leu Tyr Ser Glu Glu Ala Val Asn Gly Glu Thr<br>370 375 380 | 1152 |
| cag caa gcg cac tta cag gcg att aaa gag ctg ata gcg cgt gac aaa<br>Gln Gln Ala His Leu Gln Ala Ile Lys Glu Leu Ile Ala Arg Asp Lys<br>385 390 395 400 | 1200 |
| aac cac cca agc gtg gtg atg tgg agt att gcc aac gaa ccg gat acc<br>Asn His Pro Ser Val Val Met Trp Ser Ile Ala Asn Glu Pro Asp Thr<br>405 410 415 | 1248 |
| cgt ccg caa ggt gca cgg gaa tat ttc gcg cca ctg gcg gaa gca acg<br>Arg Pro Gln Gly Ala Arg Glu Tyr Phe Ala Pro Leu Ala Glu Ala Thr<br>420 425 430 | 1296 |
| cgt aaa ctc gac ccg acg cgt ccg atc acc tgc gtc aat gta atg ttc<br>Arg Lys Leu Asp Pro Thr Arg Pro Ile Thr Cys Val Asn Val Met Phe<br>435 440 445 | 1344 |
| tgc gac gct cac acc gat acc atc agc gat ctc ttt gat gtg ctg tgc<br>Cys Asp Ala His Thr Asp Thr Ile Ser Asp Leu Phe Asp Val Leu Cys<br>450 455 460 | 1392 |
| ctg aac cgt tat tac gga tgg tat gtc caa agc ggc gat ttg gaa acg<br>Leu Asn Arg Tyr Tyr Gly Trp Tyr Val Gln Ser Gly Asp Leu Glu Thr<br>465 470 475 480 | 1440 |
| gca gag aag gta ctg gaa aaa gaa ctt ctg gcc tgg cag gag aaa ctg<br>Ala Glu Lys Val Leu Glu Lys Glu Leu Leu Ala Trp Gln Glu Lys Leu<br>485 490 495 | 1488 |
| cat cag ccg att atc atc acc gaa tac ggc gtg gat acg tta gcc ggc<br>His Gln Pro Ile Ile Ile Thr Glu Tyr Gly Val Asp Thr Leu Ala Gly<br>500 505 510 | 1536 |
| ctg cac tca aag gag acc gac atg tgg agt gaa gag ttt cag tgt gca<br>Leu His Ser Lys Glu Thr Asp Met Trp Ser Glu Glu Phe Gln Cys Ala<br>515 520 525 | 1584 |
| tgg ctg gat atg tat cac cgc gtc ttt gat cgc gtc agc gcc gtc gtc<br>Trp Leu Asp Met Tyr His Arg Val Phe Asp Arg Val Ser Ala Val Val<br>530 535 540 | 1632 |
| ggt gaa cag gta tgg aat ttc gcc gat ttt gcg acc tcg caa agc ata<br>Gly Glu Gln Val Trp Asn Phe Ala Asp Phe Ala Thr Ser Gln Ser Ile | 1680 |

```
                    545                 550                 555                 560
ttg cgc gtt ggc ggt aac agg aaa ggg atc ttc act cgc gac cgc aaa           1728
Leu Arg Val Gly Gly Asn Arg Lys Gly Ile Phe Thr Arg Asp Arg Lys
                565                 570                 575 ccg aag tcg gcg gct tat ctg ctg cat aaa cgc tgg act ggc atg aac           1776
Pro Lys Ser Ala Ala Tyr Leu Leu His Lys Arg Trp Thr Gly Met Asn
                580                 585                 590 ttc ggt gaa aaa ccg cag cag gga gac aaa caa                               1809
Phe Gly Glu Lys Pro Gln Gln Gly Asp Lys Gln
                595                 600

<210> SEQ ID NO 3
<211> LENGTH: 603
<212> TYPE: PRT
<213> ORGANISM: Escherichia coli

<400> SEQUENCE: 3

Met Leu Arg Pro Val Glu Thr Pro Arg Glu Ile Lys Lys Leu Asp
1               5                   10                  15

Gly Leu Trp Ala Phe Ser Leu Asp Arg Glu Tyr Cys Gly Ile Asp Gln
                20                  25                  30

Arg Trp Trp Glu Ser Ala Leu Gln Glu Ser Arg Ala Ile Ala Val Pro
            35                  40                  45

Gly Ser Tyr Asn Asp Gln Phe Ala Asp Ala Asp Ile Arg Asn Tyr Val
        50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asn Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300
```

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
            325                 330                 335

Met Leu Asp Trp Ala Asp Glu His Gly Ile Val Val Phe Asp Glu Thr
                340                 345                 350

Ala Ala Val Gly Phe Asn Leu Ser Leu Gly Ile Gly Phe Glu Ala Ser
            355                 360                 365

Ser Lys Pro Lys Glu Leu Tyr Ser Glu Glu Ala Val Asn Gly Glu Thr
        370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
                420                 425                 430

Arg Lys Leu Asp Pro Thr Arg Pro Ile Thr Cys Val Asn Val Met Phe
            435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Lys Glu Thr Asp Met Trp Ser Glu Glu Phe Gln Cys Ala
            515                 520                 525

Trp Leu Asp Met Tyr His Arg Val Phe Asp Arg Val Ser Ala Val Val
            530                 535                 540

Gly Glu Gln Val Trp Asn Phe Ala Asp Phe Ala Thr Ser Gln Ser Ile
545                 550                 555                 560

Leu Arg Val Gly Gly Asn Arg Lys Gly Ile Phe Thr Arg Asp Arg Lys
            565                 570                 575

Pro Lys Ser Ala Ala Tyr Leu Leu His Lys Arg Trp Thr Gly Met Asn
            580                 585                 590

Phe Gly Glu Lys Pro Gln Gln Gly Asp Lys Gln
            595                 600

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 4
ataagaatgc ggccgctatg ttacgtcctg tagaaa                             36

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 5

-continued

```
gccctcgagt cattgtttgt ctccctg                                          27

<210> SEQ ID NO 6
<211> LENGTH: 384
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: CDS
<222> LOCATION: (13)..(369)

<400> SEQUENCE: 6
gccatggata tc gaa gtt caa ctg caa gcg tct ggc ggc ggc ctg gtt caa       51
               Glu Val Gln Leu Gln Ala Ser Gly Gly Gly Leu Val Gln
                 1               5                  10 gct ggc ggc tct ctg cgt ctg tct tgc act gct tct ggc cgt act ggc        99
Ala Gly Gly Ser Leu Arg Leu Ser Cys Thr Ala Ser Gly Arg Thr Gly
 15                  20                  25 act atc tac tct atg gct tgg ttc cgt caa gct cct ggc aaa gaa cgt       147
Thr Ile Tyr Ser Met Ala Trp Phe Arg Gln Ala Pro Gly Lys Glu Arg
 30                  35                  40                  45 gaa ttc ctg gct act gtt ggc tgg tct tct ggc atc act tac tac atg       195
Glu Phe Leu Ala Thr Val Gly Trp Ser Ser Gly Ile Thr Tyr Tyr Met
                 50                  55                  60 gat tct gtt aaa ggc cgt ttc act atc tct cgt gat aac gct aaa aac       243
Asp Ser Val Lys Gly Arg Phe Thr Ile Ser Arg Asp Asn Ala Lys Asn
                 65                  70                  75 tct gct tac ctg caa atg aac tct ctg aaa cct gaa gat act gct gtt       291
Ser Ala Tyr Leu Gln Met Asn Ser Leu Lys Pro Glu Asp Thr Ala Val
         80                  85                  90 tac tac tgc act gct act cgt gct tac tct gtt ggc tac gat tac tgg       339
Tyr Tyr Cys Thr Ala Thr Arg Ala Tyr Ser Val Gly Tyr Asp Tyr Trp
     95                 100                 105 ggc caa ggc act caa gtt act gtt tct cat ggtgagtcca agctt              384
Gly Gln Gly Thr Gln Val Thr Val Ser His
110                 115
```